US009849292B2

(12) United States Patent
Wedan et al.

(10) Patent No.: US 9,849,292 B2
(45) Date of Patent: Dec. 26, 2017

(54) MRI COMPATIBLE IMPLANTABLE MEDICAL DEVICES AND METHODS

(71) Applicant: Cardiac Pacemakers, Inc., St. Paul, MN (US)

(72) Inventors: Steve R. Wedan, Savage, MN (US); Jean M. Bobgan, Maple Grove, MN (US); Thomas W. Lloyd, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/153,189

(22) Filed: May 12, 2016

(65) Prior Publication Data

US 2016/0256695 A1 Sep. 8, 2016

Related U.S. Application Data

(62) Division of application No. 11/684,419, filed on Mar. 9, 2007, now Pat. No. 9,345,888.

(51) Int. Cl.
*A61N 1/37* (2006.01)
*A61N 1/08* (2006.01)
(Continued)

(52) U.S. Cl.
CPC ............ *A61N 1/3718* (2013.01); *A61N 1/08* (2013.01); *A61N 1/37* (2013.01); *G01R 33/286* (2013.01);
(Continued)

(58) Field of Classification Search
CPC .................................................. A61N 1/3718
See application file for complete search history.

(56) References Cited

U.S. PATENT DOCUMENTS 4,301,804 A 11/1981 Thompson et al.
4,379,459 A 4/1983 Stein
(Continued)

FOREIGN PATENT DOCUMENTS

EP 1716878 A 11/2006
JP 8112361 A 5/1996
(Continued)

OTHER PUBLICATIONS

File History of U.S. Appl. No. 11/680,267, 223 pgs.
(Continued)

*Primary Examiner* — Eric D. Bertram
(74) *Attorney, Agent, or Firm* — Schwegman Lundberg & Woessner, P.A.

(57) ABSTRACT

An implantable medical device configured to be compatible with the environment inside an MRI machine. The implantable medical device includes a housing constructed of an electrically conductive material and pulse generation circuitry within the housing for generating electrical voltage pulses. The implantable medical device further includes a first conductor that is configured to transmit the electrical voltage pulses from the pulse generation circuitry to a patient's cardiac tissue and a second conductor that is configured to provide an electrically conductive path from the patient's cardiac tissue back to the pulse generation circuitry. The implantable medical device further includes a selectively interruptible electrically conductive path connecting the pulse generation circuitry with the housing.

20 Claims, 6 Drawing Sheets

(51) Int. Cl.
 *G01R 29/08* (2006.01)
 *G01R 33/28* (2006.01)
(52) U.S. Cl.
 CPC .......... *A61N 1/086* (2017.08); *G01R 29/0814* (2013.01); *G01R 33/285* (2013.01)

(56) References Cited

U.S. PATENT DOCUMENTS

| | | | |
|---|---|---|---|
| 4,745,284 A | 5/1988 | Masuda et al. | |
| 4,991,580 A | 2/1991 | Moore | |
| 5,038,785 A | 8/1991 | Blakeley et al. | |
| 5,074,309 A | 12/1991 | Gerdt | |
| 5,217,010 A | 6/1993 | Tsitlik et al. | |
| 5,347,222 A | 9/1994 | Fox et al. | |
| 5,540,724 A | 7/1996 | Cox | |
| 5,601,607 A * | 2/1997 | Adams ................ | A61N 1/0563 607/119 |
| 5,697,957 A | 12/1997 | Noren et al. | |
| 5,759,197 A | 6/1998 | Sawchuk et al. | |
| 5,968,083 A | 10/1999 | Ciciarelli et al. | |
| 6,016,446 A | 1/2000 | Belalcazar | |
| 6,198,972 B1 | 3/2001 | Hartlaub et al. | |
| 6,427,085 B1 | 7/2002 | Boon et al. | |
| 6,641,154 B1 | 11/2003 | Vey et al. | |
| 6,925,322 B2 | 8/2005 | Helfer et al. | |
| 6,954,674 B2 | 10/2005 | Connelly | |
| 7,015,393 B2 | 3/2006 | Weiner et al. | |
| 7,020,517 B2 | 3/2006 | Weiner | |
| 7,038,601 B2 | 5/2006 | Uutela et al. | |
| 7,050,855 B2 | 5/2006 | Zeijlemaker et al. | |
| 7,076,283 B2 | 7/2006 | Cho et al. | |
| 7,082,328 B2 | 7/2006 | Funke | |
| 7,091,412 B2 | 8/2006 | Wang et al. | |
| 7,123,013 B2 | 10/2006 | Gray | |
| 7,853,318 B2 | 12/2010 | Wedan | |
| 7,873,412 B2 | 1/2011 | Wedan | |
| 8,014,856 B2 | 9/2011 | Wedan | |
| 9,345,888 B2 | 5/2016 | Wedan et al. | |
| 2002/0133204 A1 | 9/2002 | Hrdlicka et al. | |
| 2002/0163333 A1 | 11/2002 | Schlicker et al. | |
| 2003/0083570 A1 | 5/2003 | Cho et al. | |
| 2003/0140931 A1 | 7/2003 | Zeijlemaker et al. | |
| 2003/0144704 A1 | 7/2003 | Terry et al. | |
| 2003/0144705 A1 | 7/2003 | Funke | |
| 2003/0176897 A1 | 9/2003 | Stessman | |
| 2004/0088012 A1 | 5/2004 | Kroll et al. | |
| 2004/0098093 A1 | 5/2004 | Dicarlo | |
| 2004/0135571 A1 | 7/2004 | Uutela et al. | |
| 2004/0263172 A1 | 12/2004 | Gray et al. | |
| 2005/0070975 A1 | 3/2005 | Zeijlemaker et al. | |
| 2006/0155268 A1 | 7/2006 | Amir et al. | |
| 2006/0293591 A1 | 12/2006 | Wahlstrand et al. | |
| 2007/0106332 A1 | 5/2007 | Denker et al. | |
| 2007/0191914 A1 | 8/2007 | Stessman | |
| 2007/0200436 A1* | 8/2007 | Barak ..................... | H03K 3/57 307/106 |
| 2008/0147135 A1 | 6/2008 | Hareland | |
| 2008/0195180 A1 | 8/2008 | Stevenson et al. | |
| 2008/0221638 A1 | 9/2008 | Wedan et al. | |
| 2011/0084714 A1 | 4/2011 | Wedan | |

FOREIGN PATENT DOCUMENTS

| | | |
|---|---|---|
| JP | 1085344 A | 4/1998 |
| JP | 5225296 B2 | 3/2013 |
| WO | WO-03037429 A1 | 5/2003 |
| WO | WO-03101534 A1 | 12/2003 |
| WO | WO-2008106513 A2 | 9/2008 |
| WO | WO-2008112485 A1 | 9/2008 |

OTHER PUBLICATIONS

"U.S. Appl. No. 11/684,419, Final Office Action dated Oct. 1, 2014", 10 pgs.
"U.S. Appl. No. 11/684,419, Final Office Action dated Nov. 4, 2010", 9 pgs.
"U.S. Appl. No. 11/684,419, Non Final Office Action dated May 20, 2010", 8 pgs.
"U.S. Appl. No. 11/684,419, Non Final Office Action dated May 20, 2014", 9 pgs.
"U.S. Appl. No. 11/684,419, Non Final Office Action dated Jul. 30, 2015", 9 pgs.
"U.S. Appl. No. 11/684,419, Non Final Office Action dated Nov. 13, 2009", 6 pgs.
"U.S. Appl. No. 11/684,419, Notice of Allowance dated Jan. 25, 2016", 5 pgs.
"U.S. Appl. No. 11/684,419, Response filed Jan. 22, 2015 to Final Office Action dated Oct. 1, 2014", 10 pgs.
"U.S. Appl. No. 11/684,419, Response filed Feb. 4, 2011 to Final Office Action dated Nov. 4, 2010", 11 pgs.
"U.S. Appl. No. 11/684,419, Response filed Feb. 16, 2010 to Non Final Office Action dated Nov. 13, 2009", 7 pgs.
"U.S. Appl. No. 11/684,419, Response filed Jul. 13, 2009 to Restriction Requirement dated May 13, 2009", 1 pg.
"U.S. Appl. No. 11/684,419, Response filed Jul. 28, 2014 to Non Final Office Action dated May 20, 2014", 9 pgs.
"U.S. Appl. No. 11/684,419, Response filed Sep. 20, 2010 to Non Final Office Action dated May 20, 2010", 10 pgs.
"U.S. Appl. No. 11/684,419, Response filed Nov. 10, 2015 to Non Final Office Action dated Jul. 30, 2015", 10 pgs.
"U.S. Appl. No. 11/684,419, Restriction Requirement dated May 13, 2009", 5 pgs.
"European Application Serial No. 08730844.1, Examination Notification Art. 94(3) dated Mar. 19, 2010", 2 pgs.
"European Application Serial No. 08730844.1, Response filed May 20, 2011 to Examination Notification Art. 94(3) dated Oct. 11, 2010", 10 pgs.
File History of U.S. Appl. No. 11/686,159, 21 pgs.
"International Application Serial No. PCT/US2008/055127, International Search Report dated Aug. 10, 2008", 2 pgs.
"International Application Serial No. PCT/US2008/056015, International Preliminary Report on Patentability dated Apr. 23, 2008", 10 pgs.
"International Application Serial No. PCT/US2008/056015, International Search Report dated Jul. 17, 2008", 5 pgs.
"Japanese Application Serial No. 2009-551816, Office Action dated Jan. 18, 2012".
"Japanese Application Serial No. 2009-552882, Office Action dated Dec. 1, 2011".
Abi-Abdallah, Dima, et al., "Reference signal extraction from corrupted ECG using wavelet decomposition for MRI sequence triggering: application to small animals", BioMedical Engineering, [Online]. Retrieved from the Internet: <www.biomedical-engineering-online.com/content/5/1/11>, (Feb. 20, 2006), 1-12.
Fontaine, John M, et al., "Rapid Ventricular Pacing in a Pacemaker Patient Undergoing Magnetic Resonance Imaging", PACE, vol. 21, (Jun. 1998), 1336-1339.
Luechinger, Roger, et al., "In vivo heating of pacemaker leads during magnetic resonance imaging", European Heart Journal 2005;26, (2004), 376-383.
"European Application Serial No. 08731514.9, Communication Pursuant to Article 94(3) EPC dated Jan. 27, 2017", 5 pgs.
"European Application Serial No. 08731514.9, Office Action dated Nov. 2, 2009", 2 pgs.
"European Application Serial No. 08731514.9, Response filed May 19, 2017 to Communication Pursuant to Article 94(3) EPC dated Jan. 27, 2017", 13 pgs.
"International Application Serial No. PCT/US2008/056015, Written Opinion dated Jul. 17, 2008", 8 pgs.

* cited by examiner

MRI COMPATIBLE IMPLANTABLE MEDICAL DEVICES AND METHODS

CLAIM OF PRIORITY

This application is a divisional application and claims benefit of priority of U.S. application Ser. No. 11/684,419, filed Mar. 9, 2007, now U.S. Pat. No. 9,345,888, entitled "MRI Compatible Implantable Medical Devices and Methods," which is hereby incorporated by reference in its entirety.

FIELD OF THE INVENTION

The invention relates to implantable medical devices, and more particularly, to implantable medical devices that can be used during magnetic resonance imaging (MRI).

BACKGROUND OF THE INVENTION

Many different types of medical devices can be implanted within patients to provide medical therapy. One common type of implanted medical device is a cardiac rhythm management device, such as a pacemaker or an implantable cardioverter defibrillator (ICD). Cardiac rhythm management devices can be used to provide medical therapy to patients who have a disorder related to cardiac rhythm. For example, a pacemaker may be used to treat a patient exhibiting bradycardia. Pacemakers are generally configured to provide a pacing pulse as necessary to control the heart rate.

Magnetic resonance imaging (MRI) is a technique for visualizing body tissues of a patient for purposes of medical diagnosis and therapy. MRI relies on subjecting the body tissue of interest to a very strong uniform magnetic field, up to about 30,000 gauss, as well as a moderate strength but variable magnetic field of around 200 gauss. In the presence of these uniform and gradient magnetic fields, a radio frequency (RF) pulse is transmitted from a coil to the body tissue. Hydrogen atoms within the body tissue have a magnetic moment and tend to line up with the direction of the applied magnetic fields. Some of these hydrogen atoms will align facing one direction and others will align facing an opposite direction, such that most of the hydrogen atoms facing in alternating directions will tend to cancel each other out. However, a small percentage (but a significant absolute number) of hydrogen atoms will be unbalanced, or not cancelled out. The applied RF pulse tends to cause the unbalanced hydrogen protons to spin, or resonate, in a particular direction and at a particular frequency. When this RF pulse is turned off, the spinning hydrogen protons revert to their earlier, aligned position, and release their excess energy. The RF coil of the MRI machine is capable of detecting this released energy and transmitting a corresponding signal to a processor that in turn transforms the signal into an image of the body tissue. Because different tissues have different characteristic responses to the application of the RF pulse in the presence of the magnetic fields, these differences can be utilized to prepare an image showing areas of contrasting tissue types.

MRI techniques have proven to be very effective at diagnosing certain medical conditions and therefore allowing for patients to receive timely, appropriate medical therapy. However, in many cases patients having an implanted medical device are contraindicated for MRI, and therefore may be unable to benefit from the full scope of diagnostic techniques available. One problem is that the MRI can induce a current within elements of the implanted medical device. A principle known as Faraday's law states that any change in a magnetic field around a conductive loop will cause a voltage to be induced in the conductive loop, and consequently, cause a current to flow in the conductive loop. In the case of a patient undergoing an MRI procedure, the time-varying magnetic field gradients of the MRI machine create the required changing magnetic field and elements of the implanted cardiac rhythm management device form a conductive loop, resulting in a current flow. Unfortunately, this current flow can interfere with the proper functioning of the medical device.

For at least these reasons, implantable medical devices are needed that can be used during MRI examinations.

SUMMARY OF THE INVENTION

One aspect of the invention relates to an implantable medical device that is configured for use within an MRI machine environment. The implantable medical device includes a housing constructed of an electrically conductive material and pulse generation circuitry within the housing for generating electrical voltage pulses. The implantable medical device further includes a first conductor that is configured to transmit the electrical voltage pulses from the pulse generation circuitry to a patient's cardiac tissue and a second conductor that is configured to provide an electrically conductive path from the patient's cardiac tissue back to the pulse generation circuitry. The implantable medical device further includes a selectively interruptible electrically conductive path connecting the pulse generation circuitry with the housing.

Another aspect of the invention also relates to an implantable medical device. The implantable medical device includes a housing that is formed from an electrically conductive material and has pulse generation circuitry that is disposed within the housing for generating electrical voltage pulses. The implantable medical device also includes a diode that is disposed in series between the housing and the pulse generation circuitry, and also a switch that is disposed in series with the diode, where the switch is configured to selectively isolate the housing from the pulse generation circuitry.

A further aspect of the invention relates to an implantable medical device having a housing constructed of an electrically conductive material and a pulse generator within the housing for generating electrical voltage pulses. These electrical voltage pulses can be characterized by a voltage relative to an electrical reference potential of the pulse generator. The implantable medical device further includes a first conductor that is configured to transmit electrical voltage pulses from the pulse generator to a patient's tissue, and a second conductor that is configured to transmit an electrical reference potential of the patient's tissue to the reference potential of the pulse generator. The implantable medical device further includes an electrically conductive path from the reference potential of the pulse generator to the housing, where the electrically conductive path includes a resistor.

Yet another aspect of the invention relates to an implantable medical device including a housing comprising an electrically conductive material and pulse generation circuitry disposed within the housing for generating electrical voltage pulses. The implantable medical device also includes a resistor disposed in series between the housing and the pulse generation circuitry.

A further aspect of the invention relates to an implantable medical device having a housing constructed of an electrically conductive material and having a pulse generator within the housing for generating electrical voltage pulses. These electrical voltage pulses can be characterized by a voltage relative to an electrical reference potential of the pulse generator. The implantable medical device further includes a first conductor that is configured to transmit electrical voltage pulses from the pulse generator to a patient's tissue and a second conductor that is configured to transmit an electrical reference potential of the patient's tissue to the reference potential of the pulse generator. The implantable medical device is configured so that there is no electrically conductive path between the housing and the pulse generator.

Another aspect of the invention relates to an implantable medical device that includes a housing that is made from an electrically conductive material. The implantable medical device also includes pulse generation circuitry that is disposed within the housing for generating electrical voltage pulses. The pulse generation circuitry is configured to be electrically isolated from the housing at all times.

The invention may be more completely understood by considering the detailed description of various embodiments of the invention that follows in connection with the accompanying drawings.

BRIEF DESCRIPTION OF THE DRAWINGS

The invention may be more completely understood in connection with the following drawings, in which.

Figure 1:
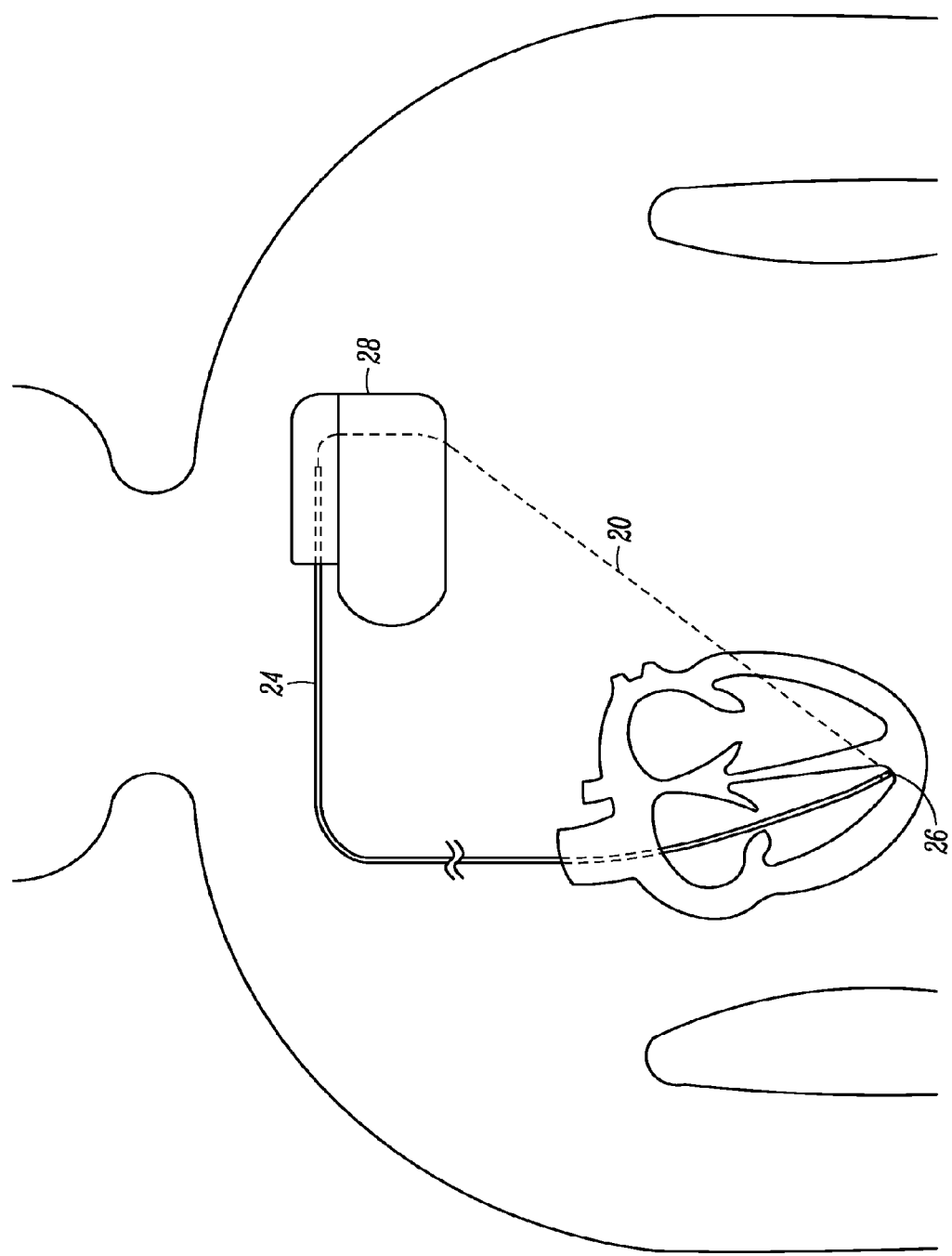
FIG. 1 is a schematic view of a conductive loop formed in an implanted unipolar cardiac pacing device.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

A variety of implanted medical devices are used to administer medical therapy to patients. One example of such an implanted medical device is a cardiac rhythm management (CRM) device. An exemplary CRM device is a pacemaker, which consists generally of a pulse generator for generating a pacing pulse and one or more leads for delivering the pacing pulse to the cardiac tissue. Some pacemakers can be configured to sense the electrical activity of the patient's heart. In some pacing modes, if the pacemaker does not detect electrical activity above a certain trigger threshold within a certain time interval, the pacemaker will deliver a pacing pulse through the one or more leads to the cardiac tissue. This pacing pulse causes the heart to beat.

Magnetic resonance imaging (MRI) is very powerful technique for non-invasively visualizing tissues of the body. Unfortunately, however, the time varying magnetic field gradients associated with MRI systems can interfere with the functioning of implanted medical devices, such as CRM devices. A principle known as Faraday's law states that a change in a magnetic field around a conductive loop will induce a voltage in the conductive loop, and consequently, cause a current to flow in the conductive loop. In the case of a patient undergoing an MRI procedure, the time varying magnetic field gradients of the MRI machine create the required changing magnetic field and the implanted pacemaker or other cardiac rhythm management device forms a conductive loop in which a current is induced. The induced currents can specifically include low frequency induced currents (LFICs) that can interfere with the functioning of the implanted medical device. For example, it is possible that LFIC could cause pacing of the heart by activating nerve or muscle cells within the heart. In this way, it may be possible for the MRI machine to inadvertently pace the patient's heart. The LFIC can also distort the waveshape of intended pacing pulses, possibly resulting in a diminished effectiveness of the pacing pulse. LFIC can further interfere with the pacemaker system's ability to properly sense cardiac activity, possibly resulting in inhibited pacing or rapid pacing.

In a unipolar pacemaker system such as that depicted in FIG. 1, a loop 20 is formed from the pacemaker internal circuitry 22, through the lead 24 to the electrode 26 in contact with cardiac tissue, and then through body tissue back to the pacemaker housing 28. The area enclosed by this loop is significant and therefore a substantial amount of LFIC can be generated within this loop by the time varying magnetic field gradients of an MRI system.

Figure 2:
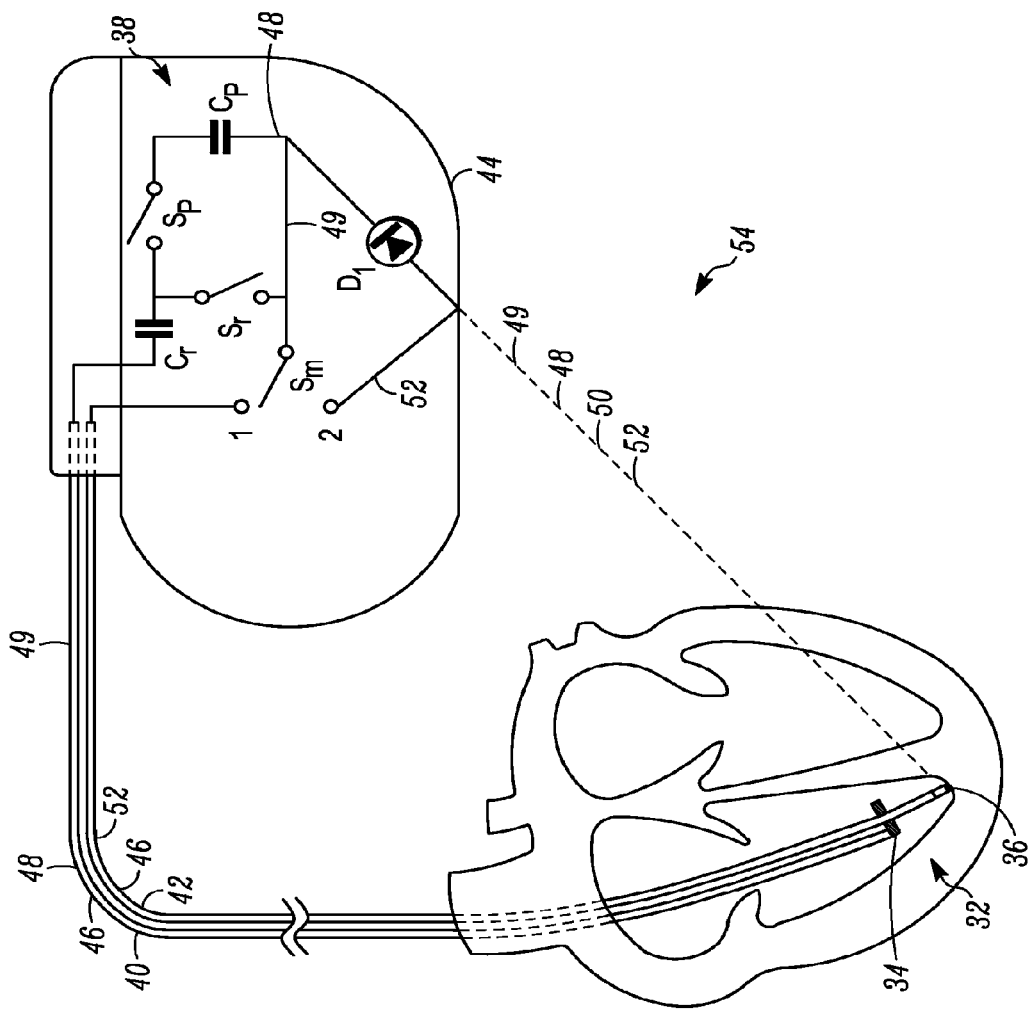
FIG. 2 is a schematic view of a conductive loop formed in an implanted bipolar cardiac pacing device.

Conductive loops can also be created in the context of bipolar pacing systems. FIG. 2 shows a simplified schematic diagram of some aspects of a typical bipolar pacemaker system. Bipolar pacemaker 54 includes a tip and ring electrode 32, where the tip electrode 34 and ring electrode 36 are each implanted in cardiac tissue, but are separated by a relatively small distance from each other. Pacemaker 54 can include various circuitries, such as pulse generation circuitry, sensing circuitry, charging circuitry, control circuitry, and the like. Sensing circuitry, charging circuitry, and control circuitry (not shown in FIG. 2) can be constructed according to principles known to those of skill in the art. In FIG. 2, pulse generator 38 includes pacing switch $S_p$, pacing capacitor $C_p$, recharging switch $S_r$, and recharging capacitor $C_r$. A pacing pulse is delivered when pacing switch $S_p$ is closed. For a period of time after the pacing pulse, pacing switch $S_p$ is opened and the recharging switch $S_r$ is closed to recharge the pacing capacitor $C_p$. When switch $S_p$ is closed, it is called the pacing window, and when switch $S_r$ is closed it is called the active recharge window. A housing 44 is provided that contains pulse generator 38. The housing 44 can be constructed of a conductive material.

As shown in FIG. 2, pulse generator 38 also includes switch $S_m$ for switching between bipolar mode and unipolar mode. To select a unipolar mode of operation, switch $S_m$ is configured to connect the pacemaker housing 44 to the pulse generator 38 circuitry. In the unipolar mode of operation, the tip electrode 34 generally serves as the cathode and the housing 44 itself serves as the anode. In FIG. 2, this occurs where switch $S_m$ connects to terminal 2 of switch $S_m$. To select a bipolar operation mode, switch $S_m$ is configured to connect conductor 42 to the pulse generator 38 circuitry. In the bipolar mode of operation, the tip electrode 34 generally serves as the cathode and the ring electrode 36 generally serves as the anode. In the embodiment of FIG. 2, this occurs when switch $S_m$ connects to terminal 1 of switch $S_m$.

In bipolar capable pacemakers, there is generally more than one conductive loop in which current can be induced. In bipolar mode, a first loop 46 is formed when either switch $S_p$ or switch $S_r$ is closed, the first loop 46 being formed either through switch $S_r$, or capacitor $C_p$ and switch $S_p$, through capacitor $C_r$, through first conductor 40 and tip electrode 34, through cardiac tissue into ring electrode 36, and through second conductor 42 to switch $S_m$. However, first and second conductors 40, 42 are generally very close together, such as disposed together within one lead. Therefore, conductive loops that include both first conductor 40 and second conductor 42 generally enclose a very small area and therefore induced current in these loops is usually insignificant.

However, conductive loops enclosing a relatively large area can also be formed by some bipolar pacemakers. Many bipolar pacemakers include an integrated circuit protection diode $D_1$. Diode $D_1$ allows current to flow from the pacemaker housing 44 into the pulse generator circuitry to the reference potential (ground) of capacitor $C_p$. This is useful to prevent the pacemaker ground from deviating from the pacemaker housing potential. However, this diode $D_1$ can facilitate the formation of conductive loops within the pacemaker. For example, when switch $S_p$ is closed, loop 48 is formed passing through capacitor $C_p$, switch $S_p$, capacitor $C_r$, conductor 40, tip electrode 34, tissue path 50, back to housing 44 and through diode $D_1$. When switch Sr is closed, loop 49 is formed passing through switch Sr, capacitor Cr, conductor 40, tip electrode 34, tissue path 50, back to housing 44 and through diode $D_1$. Loops 48 and 49 can be formed regardless of the position of switch $S_m$.

Furthermore, when switch $S_m$ is in bipolar mode, another conductive loop 52 can be formed regardless of the positions of switches $S_r$ and $S_p$. Conductive loop 52 can be formed passing through second conductor 42, electrode 36, tissue path 50 to housing 44, through diode $D_1$, and back to second conductor 42 through switch $S_m$. Loops 48, 49, and 52 each enclose an area sufficiently large to make the generation of LFIC during MRI a concern.

Figure 3:
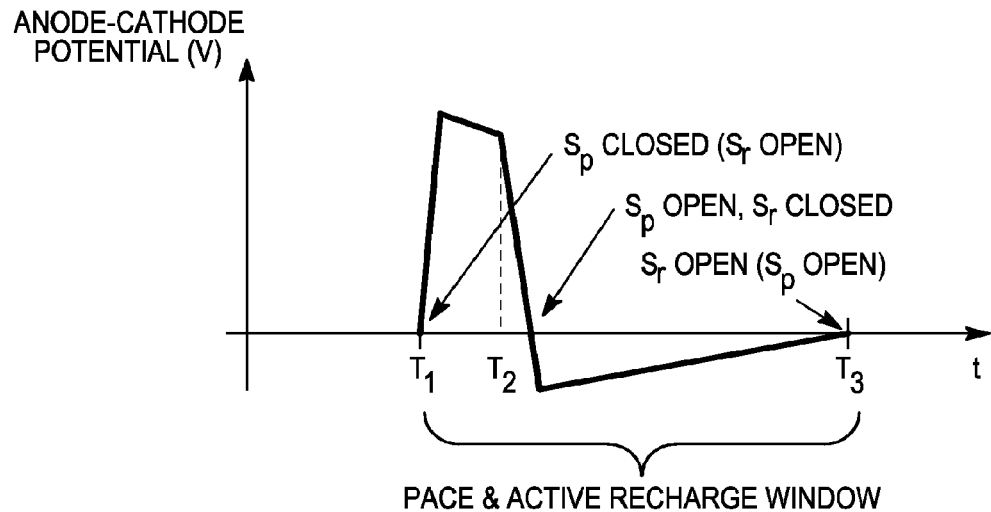
FIG. 3 is a diagram of an idealized pacing pulse.
Figure 4:
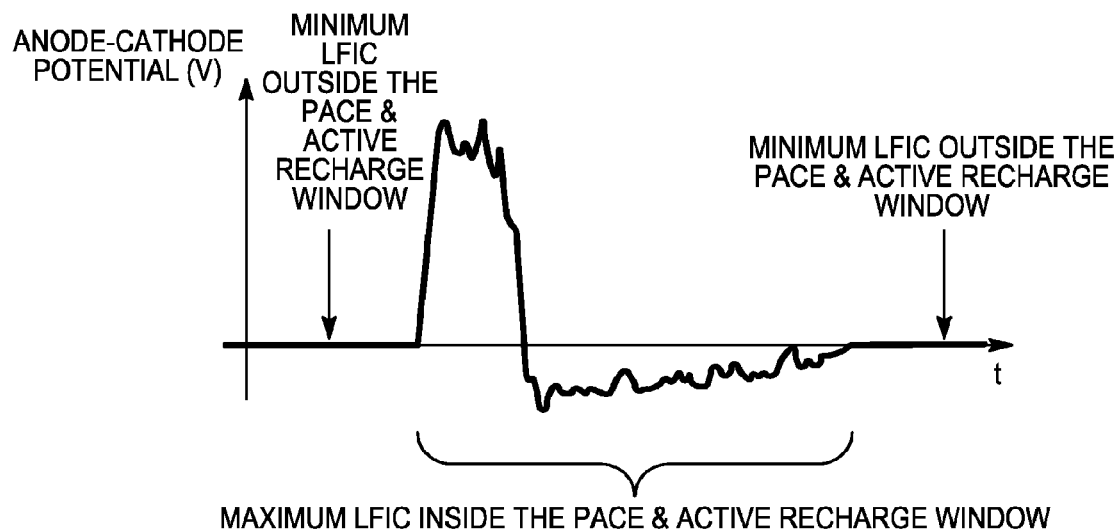
FIG. 4 is a diagram of a pacing pulse affected by low frequency induced current.

LFIC can have harmful effects on the patient. If the induced current is large enough, the current can cause activation of the heart muscle. The induced current can also cause distortion of a pacing pulse sent from the pacemaker through the leads to the heart. For example, FIG. 3 shows an example of an idealized pacing pulse. At a first time $T_1$, a pacing switch is closed causing a current pulse to be delivered through the leads for a period of time, until at time $t_2$ the pacing switch is opened and the current pulse diminishes. Also at time $T_2$, a charging switch is closed to allow charging of a capacitor until time $T_3$ when the charging switch is opened. FIG. 4 shows an example of how an idealized pacing pulse can be affected by the presence of LFIC. The current that is induced into the loop will add to or subtract from the voltage of the pacing pulse, resulting in a distorted pulse, such as that seen in FIG. 4. The LFIC may result in unreliable sensing of electrical activity in the heart, including both of the possibilities that a heart beat will not be captured and that the interference will cause a heartbeat to be captured when in fact one did not exist. In some cases, the induced distortion may cause the electrical pulse to be insufficient to capture the patient's heart. In some cases, the LFIC may be large enough in magnitude to capture the patient's heart at times other than during the pacing pulse.

For example, by forward biasing diode $D_1$, capture outside of the pace and active recharge window can be facilitated. In any case, the LFIC can interfere with the proper operation of the pacing device, possibly causing injury to the patient.

Figure 5:
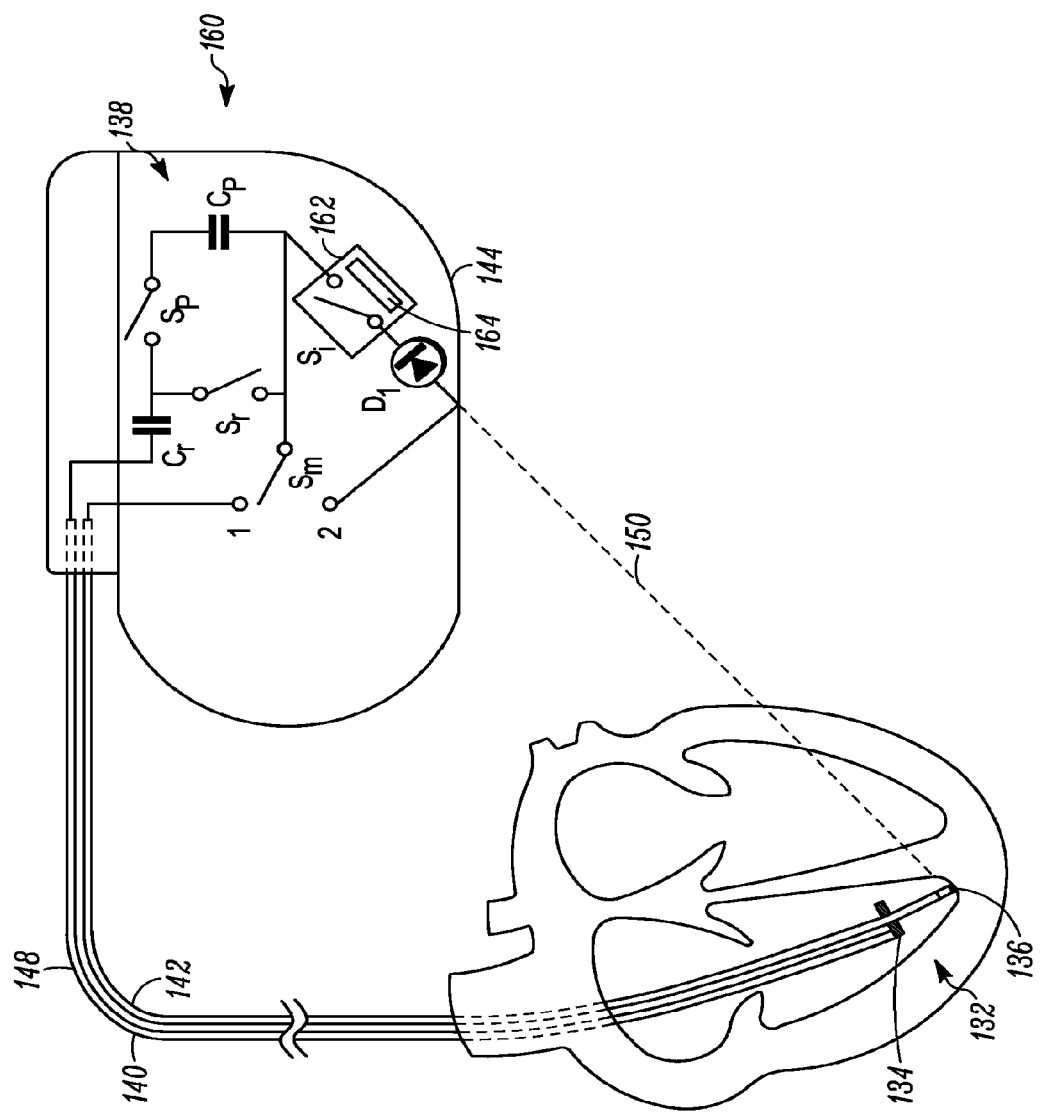
FIG. 5 is a schematic diagram of a cardiac pacing device in accordance with an embodiment of the present invention.

An embodiment of an implantable medical device configured to minimize LFIC is shown in FIG. 5. In the embodiment of FIG. 5, the implantable medical device is a CRM device. Specifically, the CRM device of FIG. 5 is a bipolar pacemaker 160 that also is capable of operating in a unipolar mode. Bipolar pacemaker 160 includes a tip and ring electrode 132, having a tip electrode 134 and ring electrode 136, a first conductor 140, and a second conductor 142. Pacemaker 160 includes pulse generator 138, which includes pacing switch $S_p$, pacing capacitor $C_p$, recharging switch $S_r$, and recharging capacitor $C_r$. Pulse generator 138 may also include other components, including sensing circuitry, control circuitry, and charging circuitry. A housing 144 is provided that contains pulse generator 138 and can be constructed from a conductive material. In the embodiment of FIG. 5, pulse generator 138 also includes switch $S_m$ for switching between bipolar pacing mode and unipolar pacing mode. Typically a medical provider such as a physician selects either bipolar mode or unipolar mode to optimize the performance of the pacemaker for an individual patient. Pacemaker 160 also includes an integrated circuit protection diode $D_1$ that allows current to flow through an electrically conductive path from the pacemaker housing 144 into the pulse generator circuitry to the reference potential (ground) of capacitor $C_p$.

Pacemaker 160 further includes switch $S_i$ for controlling LFIC during MRI. Switch $S_i$ can be in series with diode $D_1$. Although switch $S_i$ is shown in FIG. 5 as being positioned between housing 144 and diode $D_1$, switch $S_i$ can also be positioned between diode $D_1$ and pulse generator 138. Many embodiments of switch $S_i$ are usable. In one embodiment, switch $S_i$ is a transistor-type switch. In another embodiment, switch $S_i$ is a relay-type switch. In some embodiments, switch $S_i$ is configured to be opened when a patient is undergoing an MRI procedure and to be closed when a patient is not undergoing an MRI procedure. When switch $S_i$ is closed, there is an electrically conductive path from housing 144 to pulse generator 138. However, when switch $S_i$ is open and switch $S_m$ is in bipolar mode, there is no electrically conductive path from housing 144 to pulse generator 138. Thus, when switch $S_i$ is open and switch $S_m$ is in bipolar mode, there are no conductive loops enclosing a large area, and therefore the formation of LFIC is minimized or reduced.

Switch $S_i$ may include associated control circuitry 162 for controlling the operation of switch $S_i$. Many embodiments of control circuitry 162 are usable. In one embodiment, control circuitry 162 includes a sensor 164 for detecting the presence of a magnetic field associated with MRI. For example, the sensor 164 can be a magnetometer, a Hall-effect sensor, or a reed switch. Sensor 164 and control circuitry 162 are configured to detect the strong magnetic field associated with MRI, which can be on the order of 1,000 to 30,000 gauss, and to differentiate the MRI magnetic field from the earth's ambient magnetic field, which is generally less than 1 gauss. In another usable embodiment, control circuitry 162 includes a sensor for detecting the presence of low frequency induced current within loop 148. For example, sensor can be a Hall effect sensor, or can be a sensor that measures the voltage differential across a small resistor. In another usable embodiment, control circuitry 162 is configured to receive a signal, such as a telemetry signal, that is initiated outside of the patient's body, and to control switch S$_i$ in response to a received signal. For example, a person such as a physician, medical technician, nurse, or patient can initiate a first signal prior to beginning an MRI. The first signal can be initiated, for example, by activating a switch on a device. In addition, a person such as a physician, medical technician, nurse, or patient can also initiate a second signal after an MRI is completed. The second signal can also be initiated by activating a switch on a device.

In operation, switch S$_i$ is preferably placed in an open position when a patient is undergoing an MRI procedure and is preferably placed in a closed position when a patient is not undergoing an MRI procedure. In one embodiment, control circuitry 162 is configured to open switch S$_i$ in response to the detection by sensor of a magnetic field associated with MRI. In another embodiment, control circuitry 162 is configured to open switch S$_i$ in response to the detection by sensor 166 of low frequency induced current. In another embodiment, control circuitry 162 is configured to open switch S$_i$ in response to a received first signal 68 that was initiated outside of the patient's body. Control circuitry 162 is further configured to close switch S$_i$ when the sensor does not detect a magnetic field associated with MRI. In another embodiment, control circuitry 162 is configured to close switch S$_i$ when sensor does not detect low frequency induced current. In another embodiment, control circuitry 162 is configured to close switch S$_i$ in response to a received second signal that was initiated outside of the patient's body.

Figure 6:
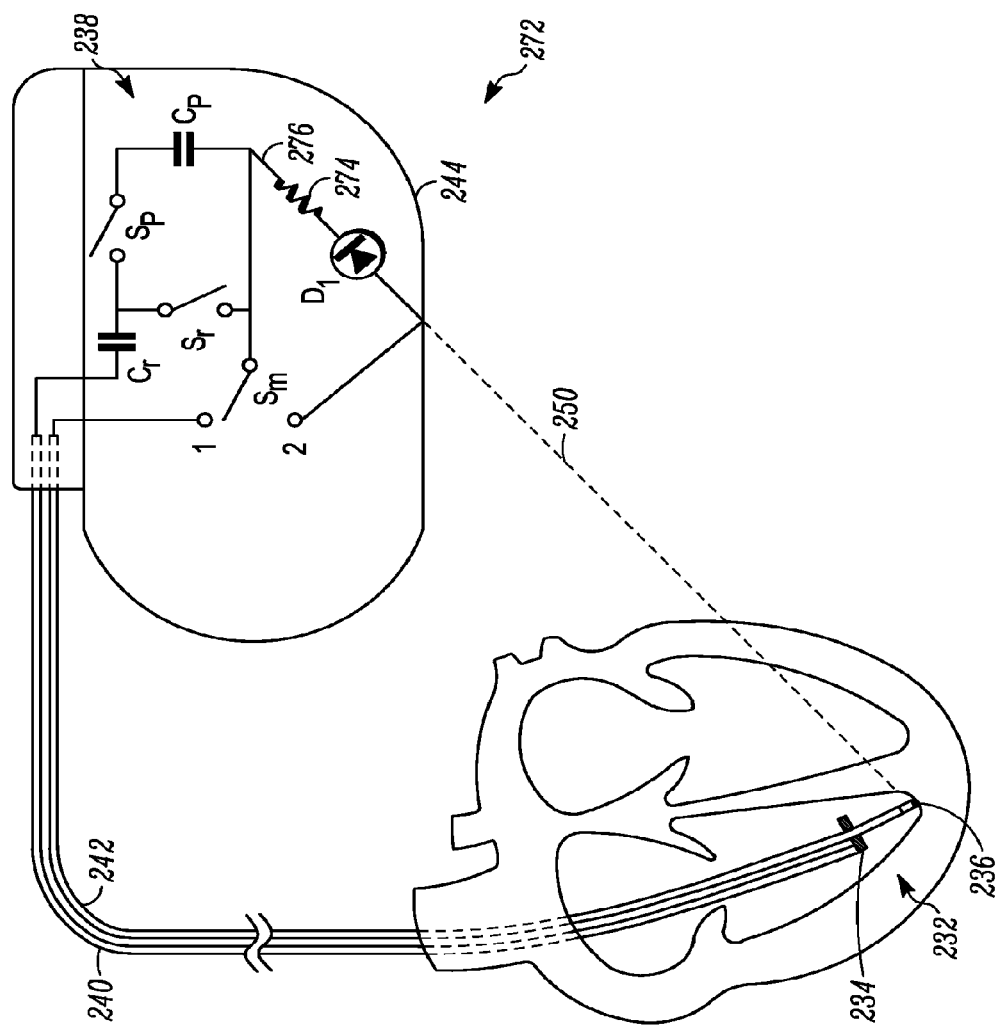
FIG. 6 is a schematic diagram of a cardiac pacing device in accordance with an embodiment of the present invention.

Other embodiments of the invention are usable. An alternative embodiment of a pacemaker 272 constructed according to the principles of the present invention is depicted in FIG. 6. Pacemaker 272 of FIG. 6 is constructed similarly to pacemaker 160 of FIG. 5. However, pacemaker 272 does not include switch S$_i$, but instead has a resistor 274 in series between pacemaker housing 244 and capacitor C$_p$. Resistor 274 can be in series with diode D$_1$. Although resistor 274 is shown in FIG. 6 as being between diode D$_1$ and pulse generator 238, resistor 274 can also be positioned between diode D$_1$ and housing 244. Resistor 274 thus forms part of a conductive loop 276 through capacitor C$_p$ and switch S$_p$ (when switch S$_p$ is closed), or through switch S$_r$ (when switch S$_r$ is closed), and through capacitor C$_r$, conductor 240, electrode 236, tissue path 250, diode D$_1$, and resistor 274. Resistor 274 preferably has a sufficient resistance to substantially limit any induced current from flowing within conductive loop 276 during an MRI procedure, yet also preferably has a small enough resistance to prevent the potential of the ground side of capacitor C$_p$ from drifting significantly from the potential of housing 244. In one embodiment, resistor 274 has a resistance between 1,000 and 300,000 ohms, and in another embodiment, resistor 274 has a resistance between 10,000 and 30,000 ohms. In operation, although a conductive loop 276 is formed and current is capable of being inducted into loop 276 during an MRI procedure, the presence of resistor 274 limits the amount of current flowing in loop 276 to an insignificant amount. For example, in one embodiment resistor 274 limits the LFIC in loop 276 to no more than 0.1 milliamps. In other embodiments, resistor 274 limits the LFIC in loop 276 to no more than 0.5 milliamps, and in further embodiments, resistor 274 limits the LFIC in loop 276 to no more than 1.0 milliamp.

Figure 7:
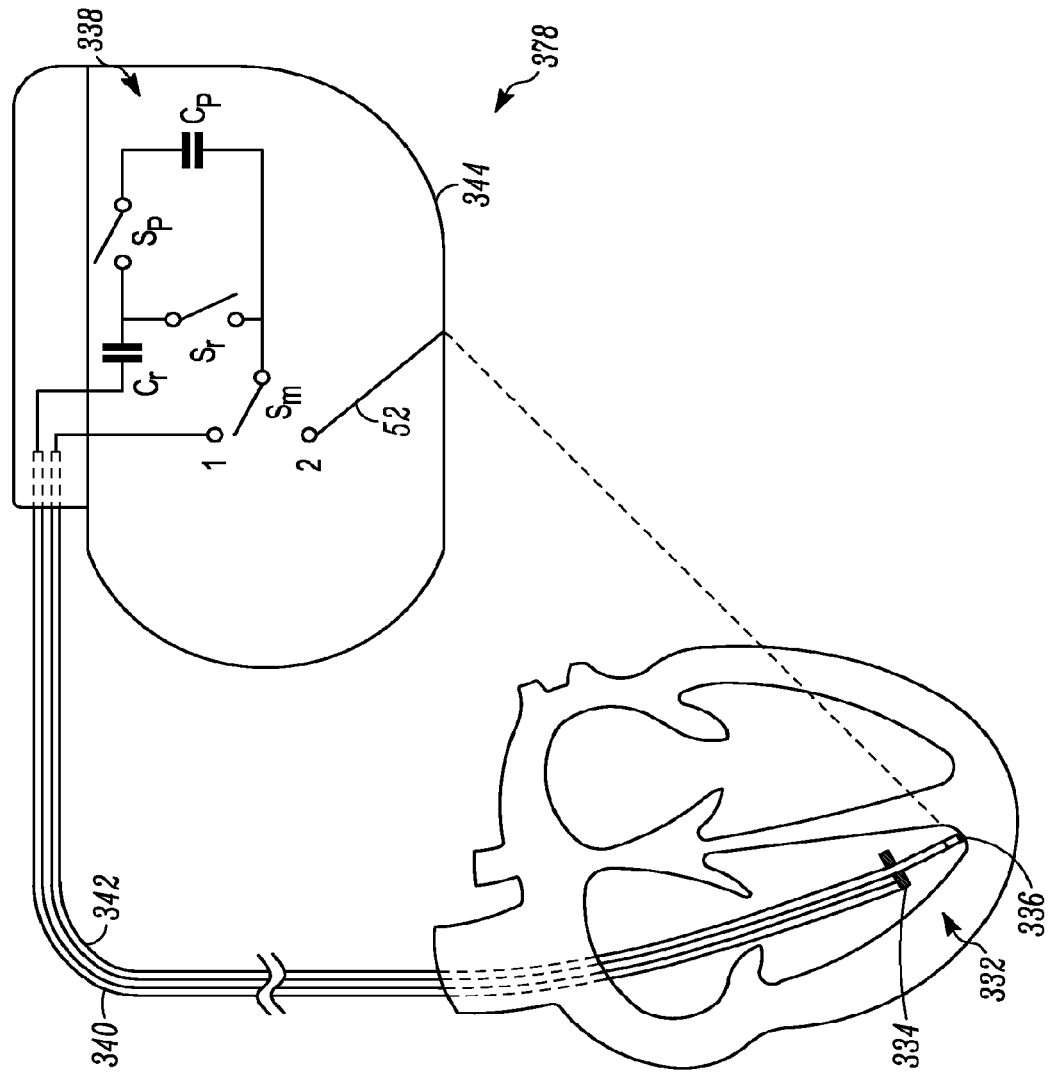
FIG. 7 is a schematic diagram of a cardiac pacing device in accordance with an embodiment of the present invention.

Yet another embodiment of the invention is depicted in FIG. 7. Pacemaker 378 of FIG. 7 is constructed similarly to pacemaker 272 of FIG. 6 and pacemaker 160 of FIG. 5. However, pacemaker 378 does not include an electrically conductive connection between housing 344 and capacitor C$_p$. When switch S$_m$ is configured to select a bipolar operation mode (that is, where switch S$_m$ connects conductor 342 to terminal 1 of switch S$_m$), there is no electrically conductive path from housing 344 to conductor 340 or pulse generator 338. Accordingly, there is no loop in which LFIC can be generated.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. An implantable medical device comprising:
    a housing comprising an electrically conductive material;
    pulse generation circuitry disposed within the housing for generating electrical voltage pulses;
    a protection diode located in series with and between the housing and the pulse generation circuitry;
    a resistor located in series with the protection diode between the housing and the pulse generation circuitry; and
    a first switch located in series with the protection diode and the resistor, the switch configured to selectively isolate the housing from the pulse generation circuitry.

2. The implantable medical device of claim 1, wherein resistor is located between the diode and the pulse generation circuitry.

3. The implantable medical device of claim 1, wherein the resistor has a resistance of 10,000 to 30,000 ohms.

4. The implantable medical device of claim 1, wherein the resistor has a resistance of 1,000 to 300,000 ohms.

5. The implantable medical device of claim 1, comprising a magnetic field sensor.

6. The implantable medical device of claim 5, comprising control circuitry configured to open the switch in response to an indication from the magnetic field sensor indicative of a magnetic field characteristic of magnetic resonance imaging.

7. The implantable medical device of claim 5, wherein the magnetic field sensor comprises a magnetometer.

8. The implantable medical device of claim 5, wherein the magnetic field sensor comprises a Hall-effect sensor.

9. The implantable medical device of claim 5, wherein the magnetic field sensor comprises a reed switch.

10. The implantable medical device of claim 5, wherein the magnetic field sensor comprises the resistor and information indicative of the magnetic field includes a voltage across the resistor established by a magnetic-field-induced current.

11. The implantable medical device of claim 1, comprising control circuitry configured to open the switch in response to detecting an electrical current that is characteristic of magnetic resonance imaging.

12. The implantable medical device of claim 1, comprising:
    a receiver configured to receive a signal transmitted from outside a body of the patient; and
    control circuitry configured to open the switch in response to the signal.

13. The implantable medical device of claim 1, comprising a second switch configured to selectively establish a bipolar lead configuration mode or a unipolar lead configuration mode for the pulse generation circuitry depending the second switch state.

14. The implantable medical device of claim 1, wherein the protection diode is included as a portion of an integrated circuit.

15. A method for operating an implantable medical device (IMD), the method comprising:
   providing, for the IMD, a housing comprising an electrically conductive material;
   providing, for the IMD, pulse generation circuitry disposed within the housing for generating electrical voltage pulses;
   providing, for the IMD, a protection diode located in series with and between the housing and the pulse generation circuitry;
   providing, for the IMD, a resistor located in series with the protection diode between the housing the pulse generation circuitry;
   providing, for the IMD, a first switch located in series with the protection diode and the resistor, the switch configured to selectively isolate the housing from the pulse generation circuitry; and
   limiting, for the IMD, a magnetic-resonance-imaging-induced current through the protection diode using the resistor.

16. The method of claim 15, comprising isolating, via the IMD, the housing from the pulse generation circuitry using a switch located in series with the protection diode and the resistor.

17. The method of claim 15, comprising opening, via the IMD, the switch in response to detecting an electrical current that is characteristic of magnetic resonance imaging.

18. The method of claim 15, comprising opening, via the IMD, the switch in response to receiving a signal transmitted from outside a body of the patient.

19. The method of claim 15, comprising providing a second switch for the IMD and selectively establishing a bipolar lead configuration mode or a unipolar lead configuration mode for the pulse generation circuitry depending the second switch state.

20. An implantable medical device comprising:
   a housing comprising an electrically conductive material;
   pulse generation circuitry disposed within the housing for generating electrical voltage pulses;
   a protection diode located in series with and between the housing and the pulse generation circuitry;
   a resistor located in series with the protection diode between the housing the pulse generation circuitry, the resistor located between the diode and the pulse generation circuitry; and
   a first switch located in series with the protection diode and the resistor, the switch configured to selectively isolate the housing from the pulse generation circuitry;
   wherein the pulse generation circuitry is otherwise electrically isolated from the housing.

* * * * *